United States Patent [19]
Friesner et al.

[11] Patent Number: 5,600,571
[45] Date of Patent: Feb. 4, 1997

[54] METHOD FOR DETERMINING PROTEIN TERTIARY STRUCTURE

[75] Inventors: Richard A. Friesner; Alessandro Monge; John Gunn, all of New York, N.Y.

[73] Assignee: The Trustees of Columbia University in the City of New York, New York, N.Y.

[21] Appl. No.: 183,298

[22] Filed: Jan. 18, 1994

[51] Int. Cl.⁶ ...................................................... G06F 17/50
[52] U.S. Cl. ............................. 364/496; 364/578; 436/89
[58] Field of Search ................................... 364/496, 497, 364/499, 578; 436/86, 89

[56] References Cited

U.S. PATENT DOCUMENTS

| | | | |
|---|---|---|---|
| 4,853,871 | 8/1989 | Pantoliano et al. | 364/496 |
| 5,260,882 | 11/1993 | Blanco et al. | 364/496 X |
| 5,265,030 | 11/1993 | Skolnick et al. | 364/578 X |
| 5,331,573 | 7/1994 | Balaji et al. | 364/578 X |

OTHER PUBLICATIONS

Gunn et al., "Hierarchical Algorithm for Computer Modeling of Protein Tertiary Structure: Folding of Myoglobin to 6.2 Å Resolution" The Journal of Physical Chemistry, V. 98 n. 2, Jan. 13, 1994, pp. 702–711.

Huston et al. "α/3₁₀—Helix Transitions in α-Methylalanine Homopeptides," Biopolymers, v. 34 n. 1, Jan. 1994, pp. 75–90.

Toma, "Protein Three–Dimensional Structure Generation with an Empirical Hydrophobic Penalty Function" Journal of Molecular Graphics v. 11, n. 4 Dec. 1993 pp. 222–232.

Holm et al., "Fast and Simple Monte Carlo Algorithm for Side Chain Optimization Proteins" Proteins, v. 14, n. 2, 1992 pp. 213–223.

Sun, "Reduced Representation Model of Protein Structure Prediction" Protein Science v. 2, n. 5, May 1993, pp. 762–785.

Unger et al., "Finding the Lowest Free Energy Conformation of a Protein is an NP–Hard Problem: Proof and Implications" Bulletin of Mathematical Biology, v. 55 n. 6 pp. 1138–1198 Nov. 1993.

*Primary Examiner*—Emanuel T. Voeltz
*Assistant Examiner*—M. Kemper
*Attorney, Agent, or Firm*—John P. White

[57] ABSTRACT

The subject invention provides a method for determining the most stable tertiary structure of a protein having a known primary structure which comprises the steps of (a) producing a reduced representation of the protein by assigning to the protein (i) all secondary structural motifs present therein and (ii) all $\phi$ and $\Phi$ dihedral angles for the amino acid residues present therein; (b) determining which conformations of the reduced representation are physically permissible, so as to determine which conformations of the protein are physically permissible; and (c) determining which of the physically permissible conformations of the protein possesses the lowest free energy, so as to thereby determine the most stable tertiary structure of the protein.

8 Claims, 11 Drawing Sheets

— Backbone Worm

━ Simplified Representation

METHOD FOR DETERMINING PROTEIN TERTIARY STRUCTURE

This invention was made with support under Grant No. P41-RR06892 from the National Institutes of Health. Accordingly, the U.S. government has certain rights in the invention.

BACKGROUND OF THE INVENTION

The determination of protein tertiary structure from computer simulation is a long-standing problem in theoretical chemistry. The complexity of the problem is due to the astronomical number of possible conformations available to a molecule of the size of a typical protein and the delicate balance of forces which stabilizes the native structure. This leads to a very complicated high-dimensional potential energy surface with a large number of local minima. Any attempt to search for the global minimum therefore must be able to efficiently explore a large number of possible configurations by overcoming local barriers which act to trap the system in a local minimum. In addition, such a search must be sufficiently accurate to distinguish the global minimum from other possible solutions at the desired level of resolution.

Detailed models with all of the protein atoms and realistic force fields, such as those commonly used in molecular modeling, are computationally much too expensive to contemplate searching the huge range of conformations necessary to discover the native topology of a complicated protein domain like myoglobin when starting from an unfolded state. Therefore, there have been numerous efforts during the past two decades to construct reduced representations of the protein, and corresponding approximate potential functions. Both lattice and off-lattice models have been employed,[1] and a variety of algorithmic approaches have been used to search for the global minimum, including exact enumeration of all states of the model, Metropolis Monte Carlo with simulated annealing, genetic algorithms, and Brownian dynamics.

Most of the prior work involved relatively small proteins at a very coarse level of representation. When dealing with a larger protein, however, many of the strategies pursued for these systems (e.g. exact enumeration) become infeasible. To treat a system such as myoglobin, additional constraints are required, at least at the current level of available computational power. One approach, taken by Skolnick and coworkers,[2] was to bias the turn regions in the direction of the native topology. While these studies provided many interesting qualitative results concerning pathways of folding, it was difficult to relate the biases to terms in the actual potential energy function; it is also unclear how one might obtain such information for a protein whose structure is not known.

A second strategy is to fix the protein secondary structure. From an energetic viewpoint, one can imagine decomposing the potential function into helix to β-sheet stabilization terms and the remaining terms representing long range hydrophobic, electrostatic, and van der Waals interactions. In practice, one might specify secondary structure either from NMR experimental data or via secondary structure prediction algorithms. Finally, it is reasonable to suppose that when secondary structure is fixed, the number of potential minima is drastically decreased, thus greatly ameliorating the multiple-minimum problem which has been a major barrier to solution of the folding problem. This idea underlies the collision-diffusion model of Karplus and coworkers concerning the folding of proteins in vivo;[3] the basic picture of formation of some secondary structure elements as an early folding event is supported by various experimental results.[4]

Early work in this direction was carried out by Warshel and Levitt[5] and by Cohen and coworkers. [6] While promising results have been reported, the methods used have not been sufficiently general to be applicable to a general protein of arbitrary complexity. To do this, according to the present invention, one must employ statistical mechanical and applied mathematical methods for minimization of functions, as opposed to construction of a small subset of configurations which is easily biased by knowledge of the correct structure.

The design of the present algorithm begins with the use of a hierarchical approach in which representations of the molecule are combined at different levels of detail in order to increase the computational efficiency of the simulation. This technique is an extension of earlier work carried out for simple polymers.[8] A Monte Carlo simulation is performed in which the trial moves consist of changes in the internal coordinates. Since each move can generate a very different structure, it is necessary to re-evaluate the energy and self-avoidance for the entire molecule at each step. However, in a compact structure (such as that of a protein) most trial moves will result in highly unfavorable configurations. Such moves can thus be rejected based on a fairly crude representation of the molecule and only those new structures which are comparable in energy in that representation need evaluated at the more detailed level.

In the case of proteins, there is a natural segmentation of the polymer chain into well-defined secondary structural units (i.e. helices to loops). In particular, α-proteins are considered which consist of relatively rigid helices connected by flexible loop regions. By constructing a model based on these structural units rather than the individual amino acids, the number of independent polymer segments is reduced by roughly an order of magnitude. The space of possible configurations of such a model is correspondingly much smaller, and can be much more effectively explored by computational means. In addition, this corresponds to the intuitive physical picture of a molecular structure which is dominated by the packaging of the helical regions. This suggests that in addition to reducing the size of the problem, the method of the present invention can simplify the potential surface by eliminating local minima which are due to finer details of the structure.

The use of the crude representation can thus allow for a more efficient exploration of the configurational space, but it lacks the detail necessary to identify correctly the global minimum. For this reason, it is important to maintain the individual residue representation and to periodically evaluate its energy so that the evolution of the configuration is ultimately determined by the more detailed model. The optimization of the crude model thus serves as a way to generate suitable trial moves for a higher level optimization of the more detailed model. With this approach, the evaluation of the lower level configurations need not be a perfect predictor of the higher level energy, but merely a good enough approximation to ensure that the more detailed calculation is only carried out for plausible changes in the structure. There will be a trade-off between the error introduced by minimizing an approximate potential function and the gain in computational speed due to less frequent evaluation of the more detailed model. The goal of the present invention is to maximize the overall efficiency by implementing the two-level representation.

The present invention provides simulations of myoglobin carried out on a 16-node partition of a massively parallel CM-5 supercomputer. The vastly increased computing power of the CM-5 (equivalent to roughly 16 IBM 550 workstations) has been essential in designing a successful methodology. However, this would have been insufficient by itself; major modifications of the potential function and computational algorithm have also been required. On the order of $10^{10}$ structure evaluations are required to produce reasonable low resolution myoglobin structures and that complex simulated annealing strategies are needed to insure the efficient traversing of potential barriers. It is within the scope of the present invention that the same algorithm can be used to fold a wide variety of proteins to the same resolution, including those containing β-sheets.

SUMMARY OF THE INVENTION

Figure 1:
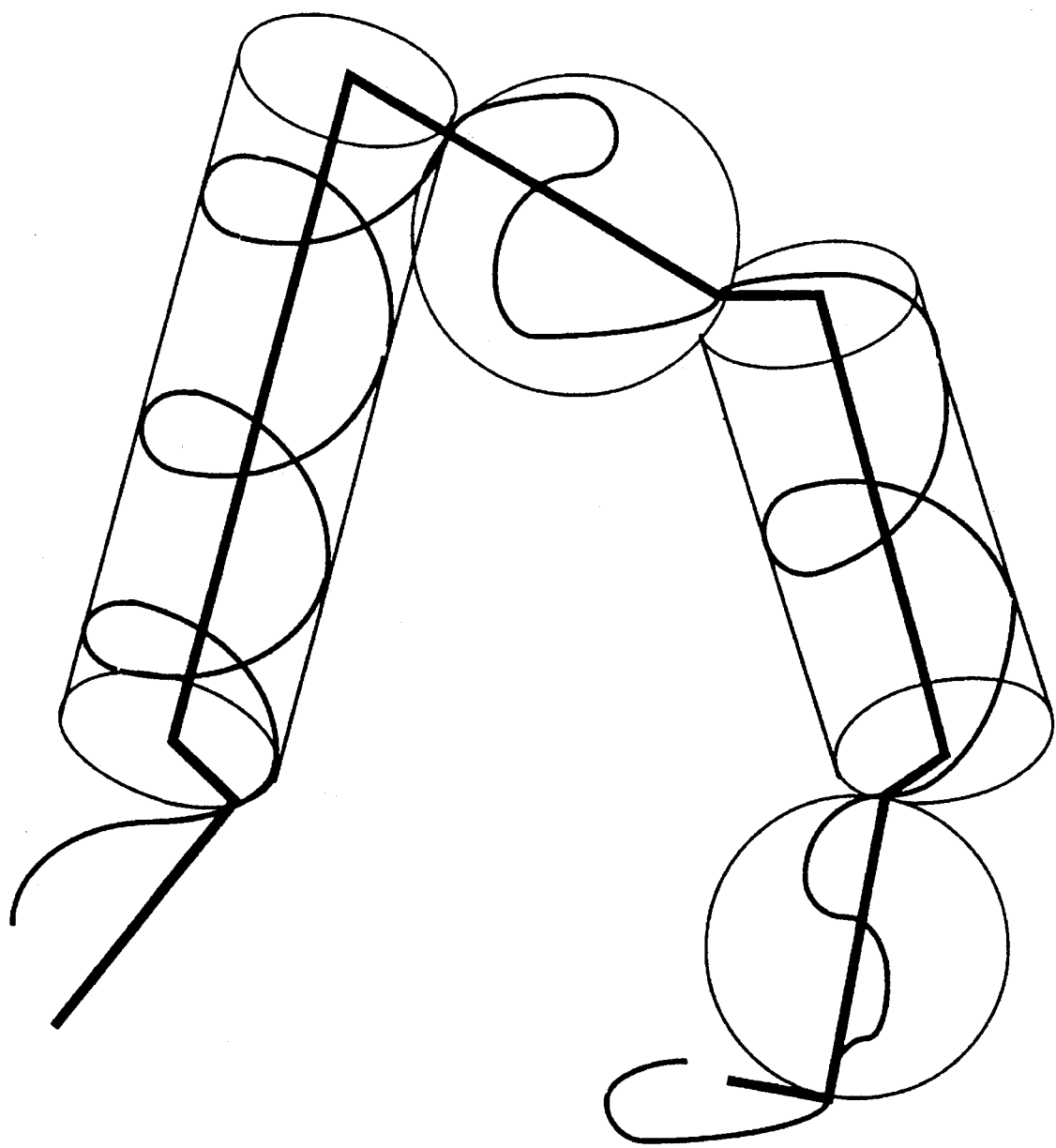
FIG. 1 shows a schematic drawing of protein backbone and enclosing cylinders and spheres which define the simplified model.

The subject invention provides a method for determining the most stable tertiary structure of a protein having a known primary structure which comprises the steps of (a) producing a reduced representation of the protein by assigning to the protein (i) all secondary structural motifs present therein and (ii) all φ and Φ dihedral angles for the amino acid residues present therein; (b) determining which conformations of the reduced representation are physically permissible, so as to determine which conformations of the protein are physically permissible; and (c) determining which of the physically permissible conformations of the protein possesses the lowest free energy, so as to thereby determine the most stable tertiary structure of the protein.

DETAILED DESCRIPTION OF THE INVENTION

The subject invention provides a method for determining the most stable tertiary structure of a protein having a known primary structure which comprises the steps of (a) producing a reduced representation of the protein by assigning to the protein (i) all secondary structural motifs present therein and (ii) all φ and Φ dihedral angles for the amino acid residues present therein; (b) determining which conformations of the reduced representation are physically permissible, so as to determine which conformations of the protein are physically permissible; and (c) determining which of the physically permissible conformations of the protein possesses the lowest free energy, so as to thereby determine the most stable tertiary structure of the protein.

As used herein, the reduced representation of a protein is a structurally simplified model of the protein suitable for computerized manipulation of the protein, and is used in determining the most stable tertiary structure of the protein.

In one embodiment, the secondary structural motif is an alpha helix. In another embodiment, the secondary structural motif is a loop.

In the preferred embodiment, the secondary structural motifs are assigned to the protein based on experimental secondary structural data. Secondary structural data include, but are in no way limited to, NMR data.

Producing a reduced representation of the protein may be accomplished, by way of example, according to the methods detailed in the Experimental Details infra.

Determining which conformations of the reduced representation are physically permissible may be accomplished, by way of example, according to the methods detailed in the Experimental Details infra.

Finally, determining which of the physically permissible conformations of the protein possesses the lowest free energy may be accomplished, by way of example, according to the methods detailed in the Experimental Details infra.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Introduction

The present invention provides a method for determining the tertiary structure of α-proteins through computer simulation. A simple model is used in which residues are described by a discrete set of φ–ψ dihedral angle conformations and the extent of α-helical regions is assumed to be known and held fixed. The invention further provides an algorithm which makes use of the assigned secondary structure to construct a representation of the molecule where helices and loops are described by cylinders and spheres respectively. Correspondence with the residue conformations is maintained by using loop geometries from a list of structures calculated using the allowed dihedral angles in segments of the appropriate length. The optimization as practiced herein consists of a Monte Carlo simulated annealing procedure combined with a genetic algorithm in which additional structures are generated by combining different members of the ensemble. The present invention provides the results of simulations carried out on myoglobin as an example in which a low-energy structure is obtained with r.m.s. deviation of 6.2 Å from the native structure. The inter-residue distance map shows that all regions of helix-helix contact are represented confirming that the overall topology of the folded structure is correct. The r.m.s. deviation of the helical regions alone is 4.1 Å, indicating that the packaging of the helices is well-reproduced by the model provided.

I—The Model

A. Geometric Representation

The protein molecule is represented by the set of backbone dihedral angles, $\phi$ and $\psi$, associated with each residue site along the chain. The conjugated peptide bonds are assumed to be planar ($\omega=180°$) and all bond distances and angles are assigned standard values based on averages observed in the Protein Data Bank. Sidechains are represented by positions of the $\beta$-carbon atoms with all other sidechain atoms omitted. The $C_\beta$ positions are assigned by assuming a standard geometry for the $C_\alpha$ center. This assignment is also performed where the residue is glycine and there is no real $C_\beta$ present. This creates a model for the backbone of the molecule which consists of $C_\alpha$ and $C_\beta$ coordinates for each residue site which are determined solely by the values of the $\phi$ and $\psi$ angles, independent of the sequence.

Local interactions are taken into account by restricting the allowed values of $\phi$ and $\psi$ to a finite number of discrete states. These states correspond to those regions of the Ramachandran plot which are observed to be populated by known structures in the Protein Data Bank. A small number of such states are sufficient to model the structure of observed proteins with reasonable global accuracy.[9] However, at that level of resolution of this model it is not necessary to restrict the dihedral angles to those which are most likely, rather it is sufficient simply to eliminate configurations which are impossible. The present invention gives this model maximum flexibility by augmenting the six dihedral states introduced by [9] with 12 additional states covering the extent of the allowed regions of the Ramachandran plot. The complete geometry of the molecule is thus specified by associating with each residue site an integer in the range from 1 to 18.

The next level of the hierarchical approach involves the specification of the secondary structure, which can be viewed as a computational technique which provides a necessary simplification of the problem regardless of whether or not it reflects the actual folding pathways of real proteins. This is achieved simply by requiring that all residue sites in the helical regions be assigned the dihedral angle state corresponding to an average $\alpha$-helix geometry (or any other state corresponding to a secondary structure motif). Consequently, all $C_\alpha$ and $C_\beta$ atoms in the helical regions will be located on identical cylindrical surfaces. The helices are thus completely specified by the cylinder axes and the radial vectors associated with the terminal sites of each helix. The simplified model is defined by constructing a polymer of the cylinder axes and radii with the loops represented by line segments connecting the endpoints of adjacent helices. A schematic drawing of a segment of a protein molecule is shown in FIG. 1 which illustrates the conventional backbone trace along with the enclosing cylinders and spheres and the points which define the simplified model. There are six independent coordinates required to specify the relative orientations in the space of two helices. These correspond to the following internal coordinates of the simplified model: the length of the loop segment, its angles with the adjacent radii, the dihedral angle between those radii, and the dihedral angles of the adjacent axes around the corresponding radii. The simplified model is thus completely specified by six parameters associated with each loop in the molecule. These parameters can be obtained for an arbitrary loop segment by calculating the positions of an additional two $C_\alpha$ atoms on each end with assumed helical geometries. These coordinates are sufficient to uniquely define the necessary cylinder axes and radii.

The values of the loop geometry parameters correspond to discrete states which are determined by the possible combinations of the dihedral angle states of the sites in each loop. For each loop, a look-up table can be calculated in advance which contains the geometries corresponding to each set of dihedral angle states. The correspondence between the two representations of the molecule is thus provided by the table, since each entry contains all the information required to construct either set of coordinates. Since the actual $C_\alpha$ and $C_\beta$ coordinates for the loop regions are not included in the simple model, the position of the loop center-of-mass relative to its endpoints and the maximum distance of any $C_\alpha$ and $C_\beta$ from the center are also calculated and included in the table. This provides for increased accuracy in checking for self-avoidance, as the loops are in general asymmetric with respect to the end-to-end vector.

In most cases, it is impractical to completely enumerate the possible loops, however for the purposes of simulation there need only be a number of entries in the tables comparable to the number of attempted trial moves. Furthermore, the tables can be recalculated at periodic intervals during a simulation. The advantage of this method lies in the ability to update the simple representation very efficiently using the loop geometries and only calculate the atomic coordinates when necessary. Furthermore, the loops can be pre-selected independently so that only those which produce locally acceptable structures are included in the tables.

Calculations were carried out with loop geometries allowed to assume continuous values during the simulation. This is equivalent to treating the cylinders as independent rigid bodies. An exhaustive search was then carried out to find the sequence of dihedral angle states which best fit the desired geometry. However, for a large number of states the quality of the fit was insufficient to provide useful matches for most of the conformations. This technique was therefore far less efficient than the use of loop lists in the simulation. In addition, the use of the all-residue coordinates at periodic intervals in the simulation is a key factor in the overall success of the model.

B. The Potential Energy Function

The primary potential function used in the simulation is a residue-based pair potential based on statistics obtained from the Protein Data Bank.[10] This is an effective free energy function where the effects of sidechain conformations and solvent are implicitly included by assuming that the structures in the Data Bank represent an equilibrium distribution of residues under the conditions found in native proteins. The potential is the of the form:

$$E = \sum_{i-j \geq 20}^{N} h_{ij}|r_i - r_j|$$

where the sum is over all pairs of sites separated by 20 or more in the sequence and the coefficient $h_{ij}$ depends on the residues at sites i and j. The residue coordinates $r_i$ are taken to be those of the $C_\beta$ atoms. The potential therefore considers only interactions between residues where it is assumed to depend only on the hydrophobic packing of the molecule and not on local structure. Since the present model has the local structure built in, a potential of this sort is well-suited to the simulation of tertiary structure. In addition, since the potential is long-range it can be used to evaluate non-compact structures found in the early stages of the simulation.

The set of pairwise hydrophobicities, $\{h_{ij}\}$, can be decomposed into a combination of single-residue hydrophobicities such that $$h_{ij} = h_i + h_j \tag{2}$$

and $$h_{ij} = h'_i + h_0 \tag{3}$$

where the $h'_i$ are the relative hydrophobicities of the residues centered around zero and $h_0$ is the net hydrophobicity which provides the overall driving force towards compactness. The $h'_i$ and an attractive interaction while hydrophilic residues will have negative $h'_i$ and be repelled. A positive value of $h_0$ ensures that the average force in the molecule will be attractive.

The analytic form of the potential also allows it to be approximated for use with the simple representation of the model. The present invention considers two secondary structure units, designated A and B, which contain respectively $N_A$ and $N_B$ sites. The pairwise energy of the two groups of residues can be written $$E_{AB} = \sum_{i=1}^{N_A} \sum_{j=1}^{N_B} (h_i^A + h_j^B)|r_i^A - r_j^B| \tag{4}$$

with the implied assumption that the two groups are separated by more than 20 sites in the sequence and are each less than 20 sites long. Neither of those conditions is necessarily true in practice; however, this approximation does not have a significant effect on the total energy of the molecule which can be written $$E = \sum_{i-j>1}^{n} E_{ij} \tag{5}$$

where the sum now runs over all pairs of non-adjacent secondary structural units. The $E_{AB}$ can be expanded in a power series around the center-center distance to give $$E_{AB} = (N_A H_B + N_B H_A) R_{AB} + \frac{1}{R_{AB}} R_{AB} \cdot (N_A D_B - N_B D_A) + O(R_{AB}^{-1}) \tag{6}$$

where $$R_A = \sum_{i=1}^{N_A} r_i^A \tag{7}$$

$$R_{AB} = R_A - R_B \tag{8}$$

$$H_A = \sum_{i=1}^{N_A} h_i^A \tag{9}$$

and $$D_A = \sum_{i=1}^{N_A} h_i^A (r_i^A - R_A) \tag{10}$$

The hydrophobicities Hi and hydrophobic dipoles $D_i$ are constants for each secondary structure unit, so that the potential in Equation 6 is a function only of $R_{ij}$. The $D_i$ can be calculated in advance in terms of local coordinates for each secondary structure unit, so that the evaluation of the dot product in the potential depends only on the loop geometries. The effect of truncating the series was investigated by calculating the quadrupolar terms. While in general the series is slowly convergent, it was found that for the helices found in real proteins the quadrupolar term is sufficiently small relative to the dipolar term to be neglected. This is consistent with the heuristic idea that the packaging of the helices in a protein is due to the segregation of opposing hydrophobic and hydrophilic surfaces.

For standard geometries of the helices, the hydrophobic dipoles can be easily calculated in local cylindrical coordinates and rotated into the molecular reference frame using the cylinder axes and radii as a 3-dimensional basis. The loop dipoles could be calculated independently and stored in the look-up table discussed above, however since the loops represent a relatively small contribution to the energy, it was sufficient to approximate all conformations of a given loop with the same dipole. This was done by projecting the sequence of residue hydrophobicities along the end-to-end vector so that the resulting dipole vector is simply proportional to it. The calculated loop centers were used to determine the $R_i$.

Figure 2:
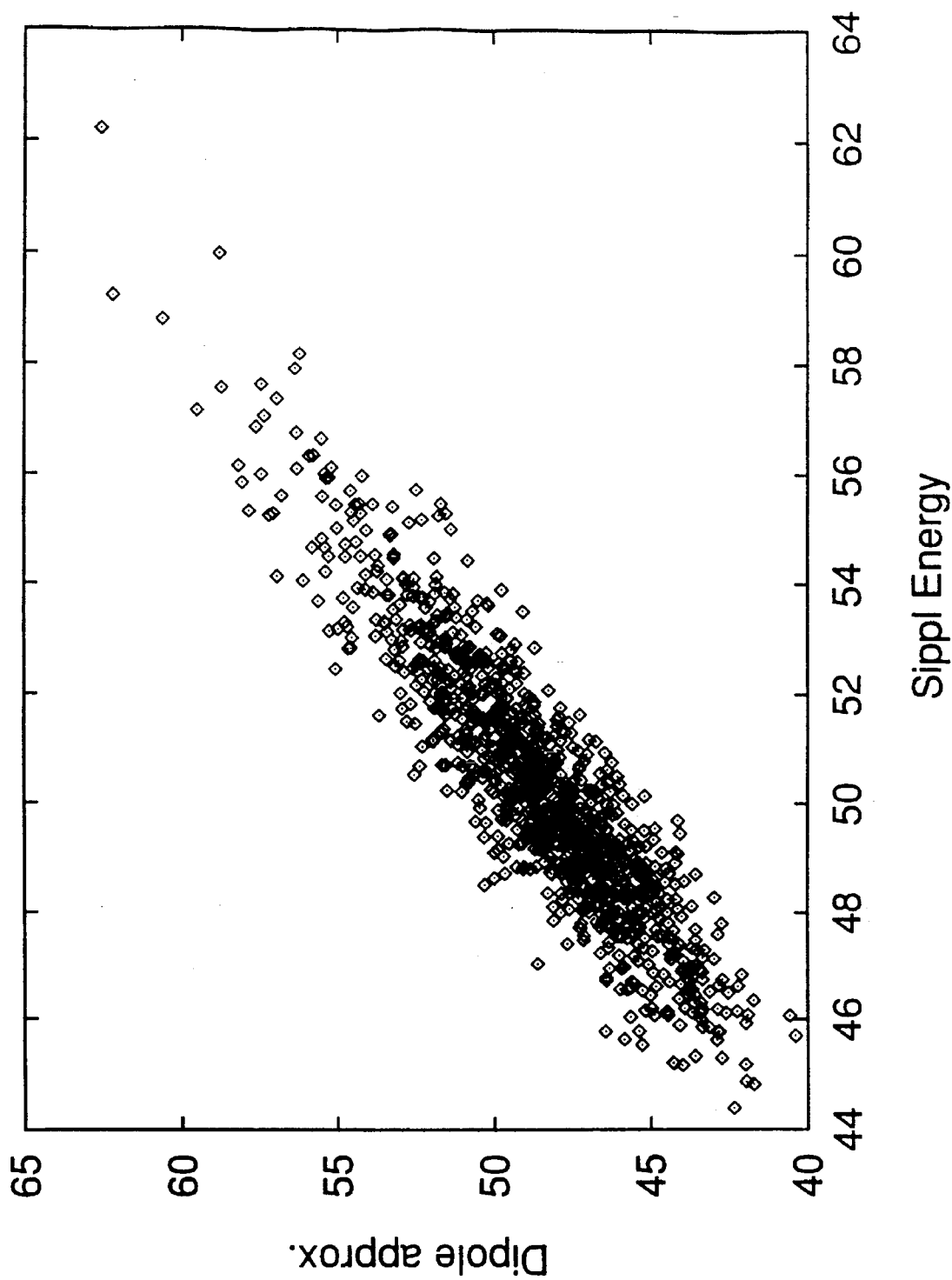
FIG. 2 shows a plot of dipole (cylinder-sphere) approximation of the Sippl energy vs. the exact calculation for a typical ensemble of structures generated by the simulation.

In practice, the accuracy of the cylinder-sphere potential function using all of the above approximations is shown in FIG. 2. The approximate energy is plotted against the exact evaluation of Equation 1 for an ensemble of structures generated by the simulation. There is a non-zero intercept due to replacing the 20-residue spacing in Equation 1 with non-adjacent secondary structure units in Equation 5. The average deviation from a straight line is much less than the overall width of the distribution, which demonstrates that the approximation is a useful predictor of the actual energy. The structures shown in FIG. 2 are the final results of a minimization, and thus represent the stage of the simulation which requires the greatest precision. For comparison, the initial configuration has an energy of 287 on the scale of FIG. 2 and the accuracy of the approximation is roughly the same over the entire range.

For the more detailed representation, the potential is evaluated directly; however, it is relatively insensitive to the details of the residue packing and thus proved to be insufficient to distinguish the correct geometry amongst comparable compact structures. In order to identify important short-range interactions between residues, an additional term is added to the potential. This term has the form $$E = \sum_{i-j \geq 8}^{N} E_{ij} \tag{11}$$

where $E'_{ij} = 0$ if $|r_i - r_j| > r_0$ and $E'_{ij}$ is a constant determined by the residues at sites i and j' when $|r_i - r_j| < r_0$. The constant coefficients were taken from the long-range portion of a complete contact potential.[11] The inclusion of the contact term creates a deep potential well for neighboring hydrophobic residues in addition to the linear attraction of the hydrophobic potential. The simulation thus minimizes a linear combination of E and E' where the relative weight of E' is another adjustable parameter. Along with $h_0$, this can be used to balance the contribution to the potential of long- and short-range interactions.

The hard-core excluded volume is accounted for by assigning a minimum allowed value to the distance between pairs of $C_\alpha$ or $C_\beta$ atoms. Additional specificity is introduced by defining different values for each possible pair of residues. These values are taken as the minimum distance observed for each pair in a survey of the Data Bank. Since there are no sidechains in the present model and the detailed shapes of the residues cannot be accounted for, this method simply excludes conformations which are expected to be impossible. It does, however, reflect the relative sizes of the various amino acids and gives rise to more realistic close-packed structures.

II—The Algorithm

A. Generation of Configurations

The initial configuration is generated with each site in the helical state to ensure a globally extended geometry with all cylinders collinear. The trial moves then consist of selecting a loop from the look-up table and rotating the cylinders in the simple model according to the new values of the internal coordinates of the loop geometry. The new configuration is checked for self-avoidance using the cylindrical surfaces containing the helical atoms and the spheres which enclose the loops. Since the packing of the residues is ultimately determined by the residue-specific cut-offs for which the cylinders and spheres lack sufficient resolution, the checking at this stage of the simulation is used only to reject structures which are impossible while still allowing those which may contain a number of overlapping residues. This allows for greater efficiency in overcoming kinetic barriers and generating compact structures by allowing the secondary structure units to 'brush' past one another, while still preventing the molecule from assuming an unphysical topology.

The loops themselves are also checked for self-avoidance prior to inclusion in the table, so that the local interactions within the spheres and between spheres and adjacent cylinders need not be re-checked in the simulation. The selection is improved by generating the $C_\alpha$ and $C_\beta$ coordinates for the first four helical residues on either side of the loop in addition to the loop residues themselves. Since some overlaps are still allowed at this stage of the simulation, the exact cut-off is not used, but rather a residue-independent minimum value which as above serves only to eliminate impossible configurations.

For those structures accepted on the basis of self-avoidance, the energy is then evaluated using the dipole approximation to the potential, and the configuration is accepted or rejected according to the Metropolis test. Since the potential is only approximate, this test is not carried out at the annealed temperature but instead at a constant 'bath' temperature which is comparable to the average error of approximation. This cycle is repeated for a number of steps and the $C_\alpha$ and $C\beta 12$ atomic coordinates are generated for the current configuration using the dihedral angle states associated with each of the loops. The energy is then evaluated using the full potential for comparison with the previous all-residue structure.

The actual number of overlapping residues is also calculated from the $C_\alpha$ and $C_\beta$ positions using the cut-off matrix. For each overlap, a constant penalty is added to the energy. This penalty is a variable parameter which ensures that the structures which contain some overlaps can still be accepted at the more detailed level and serve as intermediates in the generation of compact structures. The structure is then accepted or rejected based on the Metropolis test using the combined energy and penalty. If the move is rejected, the coordinates are returned to the previously accepted all-residue geometry, and the cycle of trial moves for the simple representation is restarted from that point to generate another trial move for the next all-residue step. In addition, the approximate energy is increased by the amount of the penalty, in order to prevent the simulation from getting stuck in a configuration where the overlap cannot be relieved and to increase the chances of overcoming local energy barriers.

The simulation thus proceeds as a nested combination of the two models, where the trial moves used in the more detailed model are in effect the results of short simulations of the simpler model.

The minimization described thus far is carried out simultaneously for a large number of structures. The minimization of the ensemble is enhanced by periodically including a step in which parts of different structures are allowed to mix in a genetic algorithm.[12] In the implementation according to the present invention, a loop is randomly chosen as a splice point. For each structure several new structures are generated by copying the loop geometries in the shorter end of the molecule from another randomly chosen structure. The two parts are then connected by inserting new loops from the table at the splice point, keeping the lowest energy structure from each series of trial loops. The number of trials is chosen so as to ensure a sufficient number of allowed structures among the hybrids. All hybrids generated from the same dominant parent are then compared and the lowest energy selected. This reduces the number of trial structures to a single child for each parent, which can then be treated as a new trial move and accepted or rejected by direct comparison using the Metropolis test. This one-to-one correspondence is useful for carrying out the calculation in parallel. The segregation of structures by the dominant parent also serves to prevent similar low-energy children of the same parent from proliferating and causing the ensemble to converge to a single structure.

The efficiency of the genetic algorithm also relies on the use of the two-level representation of the molecule. The generation of and evaluation of the hybrid structures can be carried out rapidly using the simple model. This is a significant advantage since the genetic algorithm requires the generation of a number of hybrids much larger than the size of the original ensemble. The cylinder and sphere representation is used for all minimization up to and including the selection of the lowest energy child for each parent. This selection is carried out subject to a randomly added fraction of the 'bath' temperature. Only when the new ensemble has been reduced to its original size are the all-residue structures generated and the full energies evaluated. The final comparison with the original parents is thus carried out using the more detailed representation, as is the case with the Monte Carlo minimization.

B. Use Of Parallel Computation

The simulation described herein was carried out on a 16-node Connection machine which consists of four vector processors per node each with 2MB local memory. Since calculations involving local memory are much faster than communication between nodes, the algorithm has been designed to take advantage of data-parallel execution. The Monte Carlo minimization is carried out by performing the same operations simultaneously for all structures in the ensemble. The genetic algorithm is structured in a similar manner by using the same splice point for all hybrids in a particular cycle. The hybrids are generated by performing a random cyclical shift on the coordinate arrays so that each can be simultaneously overwritten with the same offset. The hybrids thus created are broadcast into a larger array such that they remain on the same processor as the dominant parent. The hybrids generated by a number of different offsets are collected into this array, and the loop insertion and minimization cycles are carried out for this larger ensemble exactly as in the case of the Monte Carlo cycles. The reduction of this ensemble to a single child per parent again involves only local memory on each processor, and the subsequent all-residue comparison identical to that performed in the regular Monte Carlo steps.

The lookup table of loop geometries is generated by simultaneously constructing an array of random loops of a given length. This array is several times larger than the desired lookup table, so the calculation can simply be repeated until the necessary fraction of the loops are accepted. This method has the advantage of performing all the time-consuming chain-building, overlap-checking, and geometry calculations using the maximum available vector length. The loop table is distributed across all nodes on the machine, so in order to avoid inter-node communication the loop lookup in the simulation is restricted to only those loops currently in local memory. After a number of iterations the loop table is circularly shifted so that a new set of loops resides on each processor. After the table has been shifted 64 times (equal to the number of processors) the entire table is regenerated. The cycles are chosen so that each structure will only sample a fraction of the loops in the table before it is replaced, but since there are so many structures on each processor each loop will on average have been used a number of times.

C. Simulated Annealing And Directed Minimization

The principal minimization method is the slow reduction of the temperature of the simulation from an initial high value comparable to the width of the distribution of energies in a typical ensemble to a final low comparable to the typical spacing between structures in an ensemble. Since the energy units in the simulation are arbitrary, this temperature is solely a parameter which is introduced in order to optimize the minimization. The limits are chosen so as to span the range of energy barriers encountered in the simulation. The temperature is reduced exponentially by multiplying it by a constant factor periodically during the simulation. Since the final temperature is much lower than the accuracy of the dipole approximation to the potential, the 'bath' temperature is used in order to prevent the simulation from getting stuck in a local minimum of the approximate potential.

In addition to simulated annealing, an important part of the algorithm consists of increasing the overlap penalty during the course of the simulation. An initially large value of the penalty would be highly inefficient since most of the structures generated from the cylinder and sphere geometries will contain overlaps and would thus be immediately rejected. This kinetic barrier can be removed by lowering the penalty in order to generate compact structures and then gradually turning it back on in order to select out those with the fewest overlaps. Because the cylinder and sphere representation serves to eliminate structures with unavoidable overlaps, most can be relieved with only minor changes in the geometry, and increasing the overlap penalty can generate structures in which all overlaps have been removed with little or no increase in the energy. This technique is similar in principle to the σ-fluctuation method for accelerating Molecular Dynamics calculations.[13] However, in this case it is not the hard-core distance that is varied, but simply the arbitrary energetic penalty imposed for violating it. Similar ideas in which the potential function itself is continuously smoothed out as a means of locating the global minimum have also been introduced.[14]

The potential function itself can also be annealed by continuously varying the net hydrophobicity and the coefficient of the contact potential. Since the relative hydrophobicities are balanced between attractive and repulsive terms, either the net hydrophobicity or contact potential is needed in order to stabilize compact structures. The contact potential contains very deep energy wells and thus creates additional local minima in the potential surface. For this reason, it has been found that favoring specific local contacts during the simulation impedes the minimization.[7] Conversely, the net hydrophobicity is a uniform driving force which favors all structures with low radii of gyration independent of sequence. This therefore makes it difficult to distinguish among similar structures and impairs the selectivity of the native structure. The procedure used in this invention involves a linear crossover from a larger net hydrophobicity at the beginning of the simulation to a large contact potential at the end. This serves to first generate an ensemble of compact structures and then gradually sort them based on sequence-specific interactions. While the temperature annealing controls which local barriers the system is able to cross, the annealing of the potential parameters also controls the types of barriers which exist in the potential surface itself. The contact potential is necessarily neglected by the approximate potential used in the cylinder and sphere model. However, at the stage of the simulation where the contact potential becomes important the structures are already compact and the simple model is relatively insensitive to the structure, and merely serves to eliminate unfolded and topologically impossible trial moves.

The present invention provides methods to aid in the further refinement of a minimized ensemble of structures. The first technique involves sorting the loop geometries into bins and restricting the loop tables to only those loops which fall in the same bins as those already occupied in the ensemble. This is based on the observation that some parts of the structure become relatively constant throughout the ensemble, and further improvement is due to small changes in the geometry. Restricting the loop table thus serves to eliminate trial moves with greatly differing geometries which have virtually no chance of being accepted. It also greatly increases the number of possible trial loops in the region of parameter space close to the existing geometries since the same number of loops are generated for the table, but they are selected from a limited number of bins. Some computational effort is thus shifted to the generation of the loop tables with a relatively low acceptance rate where many iterations may be required to fill up the tables. The result, however, is a minimization where the trial moves are known to result in relatively small changes in the structure.

Additionally, the minimization can be accelerated by discarding higher energy structures and replacing them in the ensemble with extra copies of low-energy structures. Since many of the low-energy structures tend to be similar, this has the advantage of further narrowing the range of desired loops and combining different variations of similar structures to generate a more highly optimized version. Combined with the genetic algorithm, this can lead to an ensemble which is dominated by a small number of distinct structures.

In order to continue effective minimization, it is important to maintain the diversity of the ensemble of structures. To achieve this, the initial ensemble can be selected from not just the lowest energy structures but also higher energy structures which are close in r.m.s. deviation to a number of the low-energy structures. Since the low-energy structures tend to consist of clusters of structures with similar topologies, this procedure can identify other members of the ensemble which fall into the same dominant clusters. Although these individual structures may be high in energy, they may contain highly favorable segments which can lead to improved structures when combined via the genetic algorithm with similar structure already lower in energy.

III—Results

The initial tests of the algorithm were conducted using myoglobin (1MBO in the Protein Data Bank notation) as a well-known example of an α-helical protein with a non-trivial folded structure. In the present model, myoglobin consists of eight helices connected by seven loops, with the terminal loop regions neglected leaving 146 residues for which are assigned dihedral angle states. The end loops are not included since their representation using the loop geometries described earlier would not make sense. Since these loops are short, three and four residues, it is assumed that they can be added on at a later stage in a similar manner as the sidechains. The prosthetic heme group is also neglected, which is not expected to significantly alter the native conformation.

Simulations were carried out consisting of nested cycles of 100 cylinder and sphere MC steps, 16 all-residue steps, 4 genetic algorithm steps, and 100 loop table steps. This corresponds to totals of 640,000 cylinder and 6,400 all-residue steps and 400 genetic algorithm steps. Additionally, each genetic algorithm step included 32 hybrids for each structure and 100 trial loops for each hybrid. For an ensemble of 1024 structures, this is equivalent to a total of roughly $2 \times 10^9$ different geometries evaluated. This takes a little less than 24 hours on the Connection Machine for a net speed of over 20,000 evaluations/second. The loop tables consisted of 16,384 geometries for each of the seven loops.

The effectiveness of the two-level simulation can be demonstrated by comparing results obtained using different variations of the algorithm for the same amount of computing time. Results from a series of limiting simulations are summarized in Table I, where all simulation parameters are identical except for the specified changes and attempts to make the total running times roughly the same. Here it can be seen that Monte Carlo simulated annealing with the combination of the cylinder-sphere and residue-based models clearly outperforms either one used individually. The more detailed model (Run A in Table I) gives better results than the simple model alone (Run B) even though the added computational effort greatly reduces the number of steps that can be carried out. With the combined algorithm (Run C), most of the time is spent evaluating the simple model resulting in a much greater number of configurations searched, but the accuracy of the more detailed model is retained, even with relatively infrequent evaluations.

structures which contain large numbers of overlaps. These results are anomalous, since further refinement to remove these overlaps generally results in much higher energies. Other tests have shown that the combination of the Mote Carlo and genetic algorithm methods (Run E) generally provides a greater number of low-energy native-like structures than either method used alone.

The importance of the slow annealing of the temperature and the gradual inclusion of the energetic penalty for overlapping residues can also be demonstrated by comparison with limiting examples, also summarized in Table I. In the first case (run F) the final temperature was reduced by a factor of 100. This has the effect of shortening the high-temperature part of the annealing and finishing the simulation with what is essentially straight minimization leading to a final ensemble which is relatively constant. The final ensemble is essentially the same as in the previous case, however with a great number of remaining overlaps. This suggests that the slower annealing is important in overcoming local barriers and retaining enough flexibility to smoothly enforce the constraints. An example is also given (Run G) where the cylinder and sphere cut-off distances are chosen to eliminate almost all potential overlaps and the overlap penalty is set to a prohibitively large value. The resulting simulation proceeds with all overlaps eliminated by the second iteration of the outer loop. The results confirm that the simulation becomes trapped at higher energy configurations and fails to produce the same final optimized results.

Processing times are also reported in Table I to indicate the relative computational effort of the different parts of the simulation. Comparison of Runs A and B shows that the residue-based model requires roughly 30 times more CPU time than the cylinder-sphere model to construct and evaluate each structure. In the combined simulations the residue-based calculation is performed every 100 cycles so that it requires only one quarter of the total time, as shown by Run C. The genetic algorithm only uses the residue-based calculation for one out of 32 hybrids, resulting in an overall ratio of 3200:1 in Run D. The reason for the increased efficiency in that case is the use of a longer vector length in the calculations reducing the overhead associated with the

TABLE I

Summary of simulation results for a series of test cases. See text for description of conditions.

| Run | Ave. energy (arb. units) | Low energy (arb. units) | Ave. deviation (Å rms) | Low deviation (Å rms) | Ave no. of overlaps | Comput. speed (struc/sec) |
|-----|--------------------------|-------------------------|------------------------|-----------------------|---------------------|---------------------------|
| A   | 51.1 | 35.4 | 13.3 | 7.4 | 3.5  | 580    |
| B   | 76.0 | 44.5 | 16.9 | 9.4 | 16.0 | 16,500 |
| C   | 45.6 | 27.2 | 12.7 | 6.0 | 3.4  | 12,300 |
| D   | 35.3 | 17.4 | 11.7 | 7.2 | 1.9  | 43,800 |
| E   | 37.2 | 24.9 | 11.9 | 6.6 | 1.6  | 20,700 |
| F   | 37.0 | 24.0 | 11.9 | 6.0 | 2.4  | 23,800 |
| G   | 45.4 | 37.7 | 11.8 | 7.3 | 0.0  | 23,300 |

The genetic algorithm (Run D) was also tested without any intervening Monte Carlo steps. Because of the generation of many hybrids at each step, this method samples the greatest number of configurations. However, its accuracy is limited by the fact that the residue-based potential is only used at the conclusion of the cycle. The main advantage of the genetic algorithm is that it exchanges favorable segments between different structures and thus creates a more tightly bunched ensemble of similar conformations. This leads to a slightly lower average energy, but with very low energy parallel processing. This is close to the maximum speed available with the present program. The speed of the Monte Carlo step can also be improved by going to a larger ensemble of configurations, but at the expense of greater time required to complete the annealing cycle and limitations in the total available memory. The loop list generation steps also take advantage of the large vector length and only take a few percent of the total time in these examples. Runs E–G were carried out using the same version of the program and thus the difference in the timing reflect typical variations due to the overall load on the machine. For comparison, current methods for carrying out sophisticated calculations using an explicit all-atom description of the molecule typically take on the order of a second for a single molecular dynamics iteration.

The optimization of and the annealing of the net hydrophobicity and contact potential are unfortunately less systematic since the results of the simulations using different potential functions are harder to compare. The results depend on knowing how the native energy compares to the rest of the distribution and selecting the parameters which lead to lowest r.m.s. deviation configurations. The values used for the results shown here were selected by trial and error. However, the simulations appear to be relatively insensitive to the actual values within a reasonable range.

Figure 3:
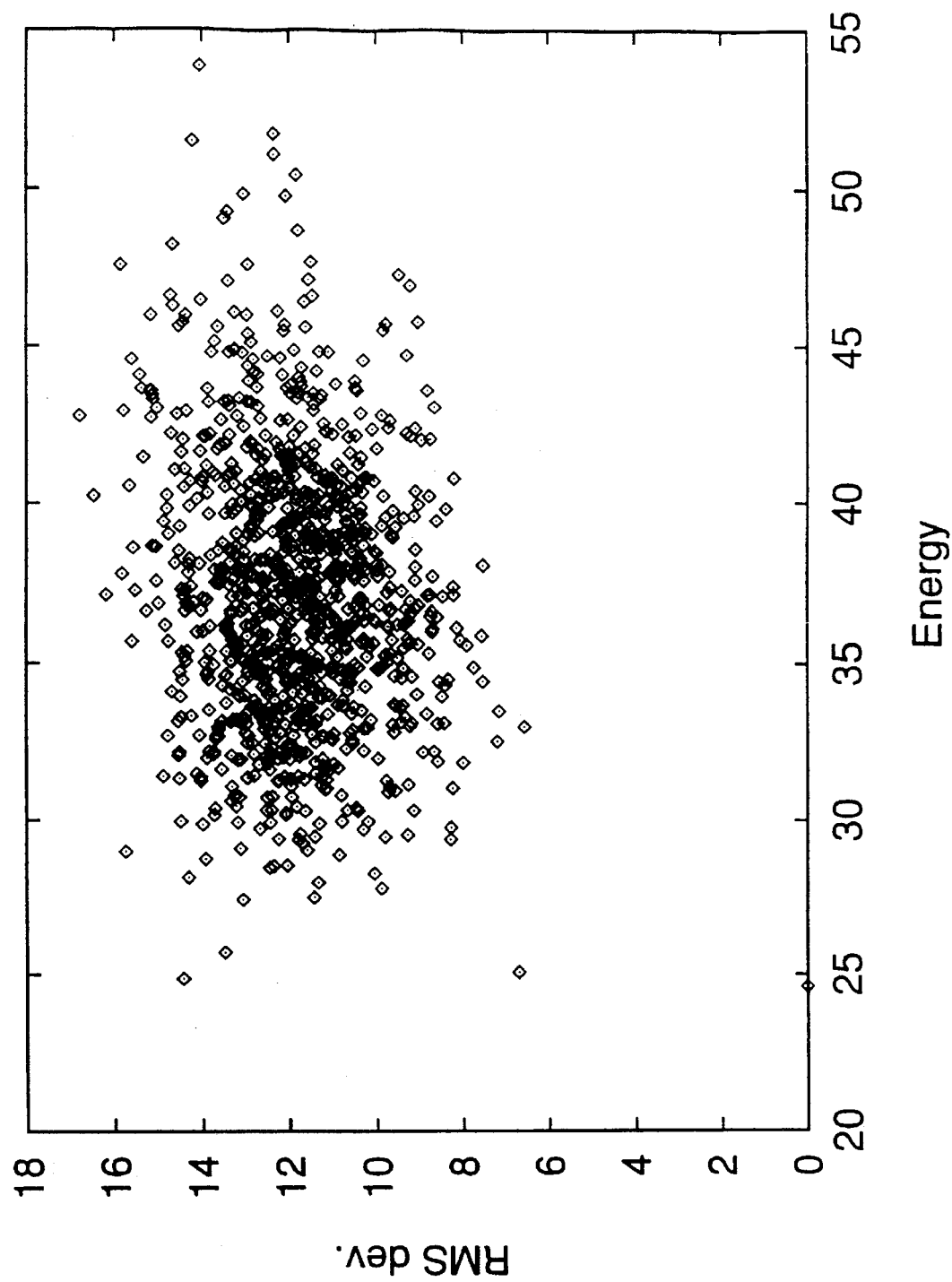
FIG. 3 shows an ensemble of structures plotted with r.m.s. deviation vs. total energy. Each point corresponds to a distinct conformation generated by the simulation. The native energy is shown with zero deviation for reference.
Figure 4:
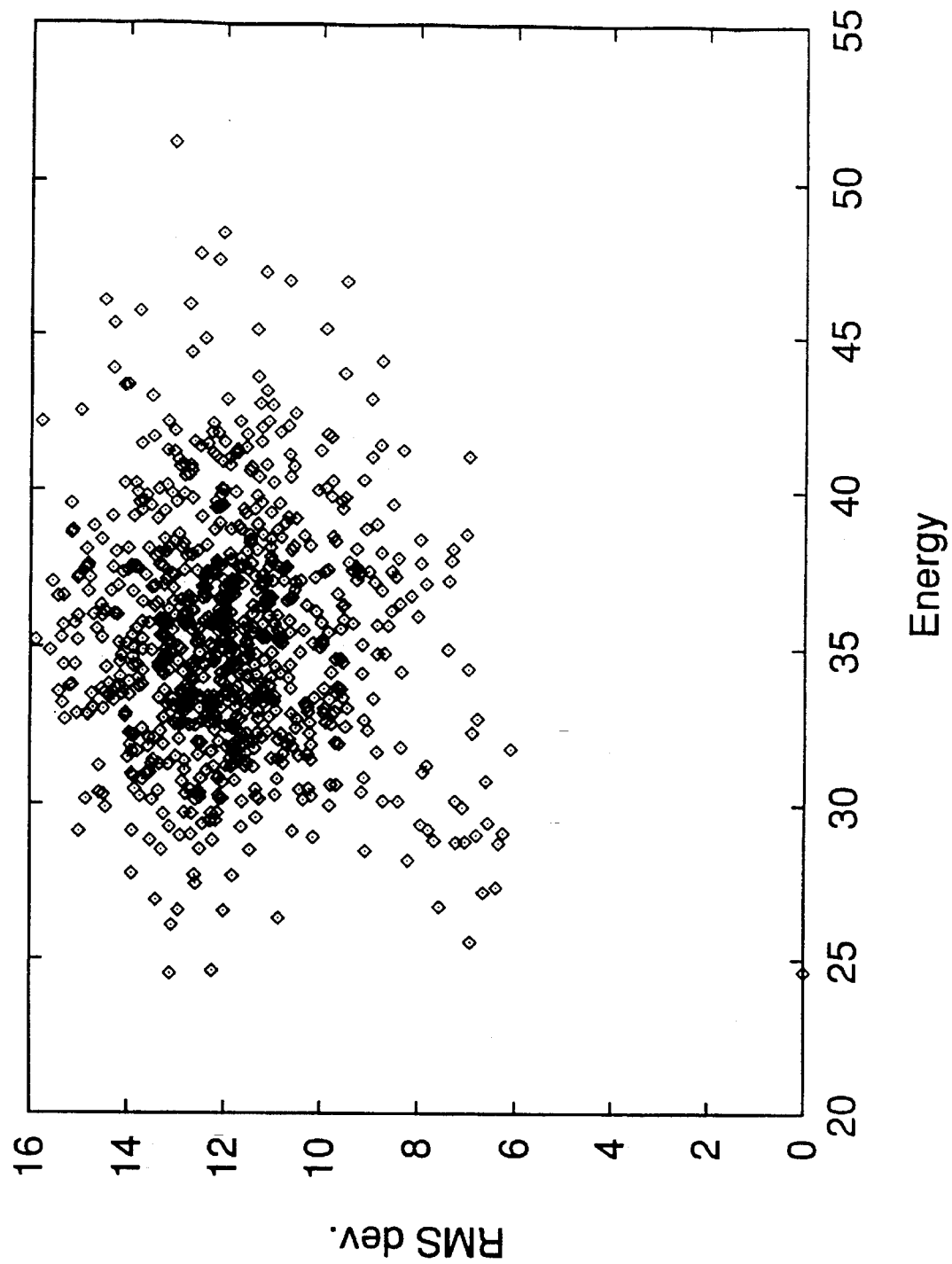
FIG. 4 shows an ensemble of structures plotted with r.m.s. deviation vs. total energy, as in FIG. 3.

The complete final distribution from Run E described above is plotted in FIG. 3 with each structure identified by total energy and r.m.s. deviation. The first step in the refinement of the ensemble consisted of selecting the lowest energy structures (32/1024) and continuing the simulations with restricted loop lists and a greatly increased overlap penalty. The resulting ensemble is shown in FIG. 4. The fraction of structures containing overlaps was reduced to roughly 5% with little change in the overall distribution. More importantly, the number of native-like structures with low energies has been increased from one in FIG. 3 to a substantial number in FIG. 4. This was found to occur even if the single good structure from the initial run was excluded, indicating that the same loops are found in many of the other structures. In addition, since the initial ensemble for the refinement consisted of 32 copies of each structure, many of the low-energy structures occur several times in the final ensemble as well. The structures with low energy and low r.m.s. deviations were also found to be duplicated more than structures at higher r.m.s. deviation.

The conclusion of these results is that there does indeed exist a shallow minimum in the global potential energy surface to the native-like topology and that once it is reached it forms a stable basin of attraction for the ensemble. However, it is also clear from the distribution in FIG. 4 that the same is true for another group of structures which are very different from the native. Additional tests confirm the structures with low energy and high r.m.s. deviation are similar to one another with a distinct folded topology.

Figure 5:
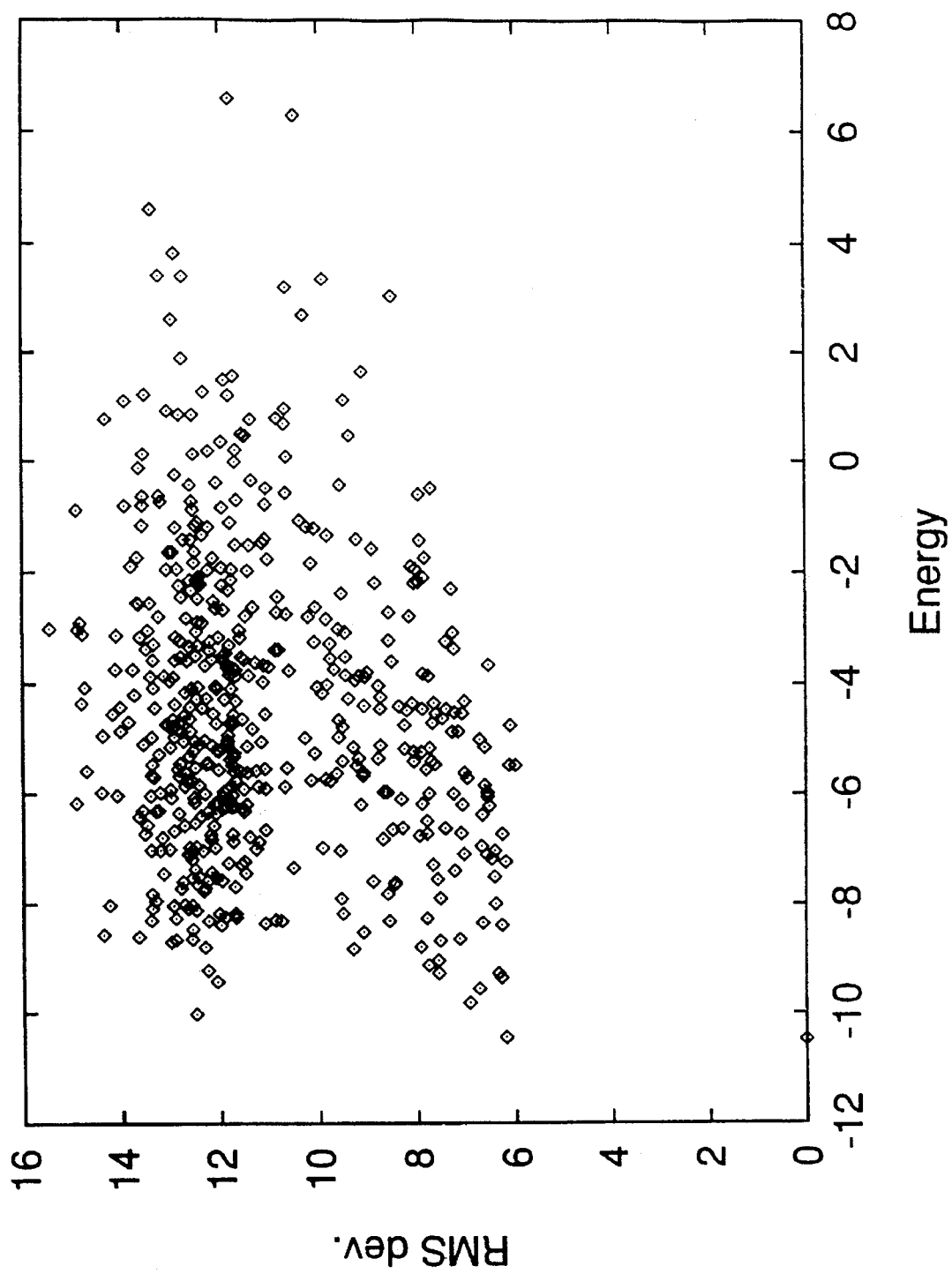
FIG. 5 shows an ensemble of structures plotted with r.m.s. deviation vs. total energy, as in FIG. 3.

Further refinement was carried out using the cluster selection algorithm where the initial ensemble consisted of the distinct low-energy structures as well as an additional 32 structures for which the greatest number of the low-energy structures were identified as structurally similar. The results of this final refinement are shown in FIG. 5. In addition, the net hydrophobicity was changed slightly resulting in a different energy scale in which the size-dependent part of the potential was mostly removed in order to better differentiate among the remaining structures. At this stage the ensemble is clearly split into two competing topologies with comparable energies.

Figure 6:
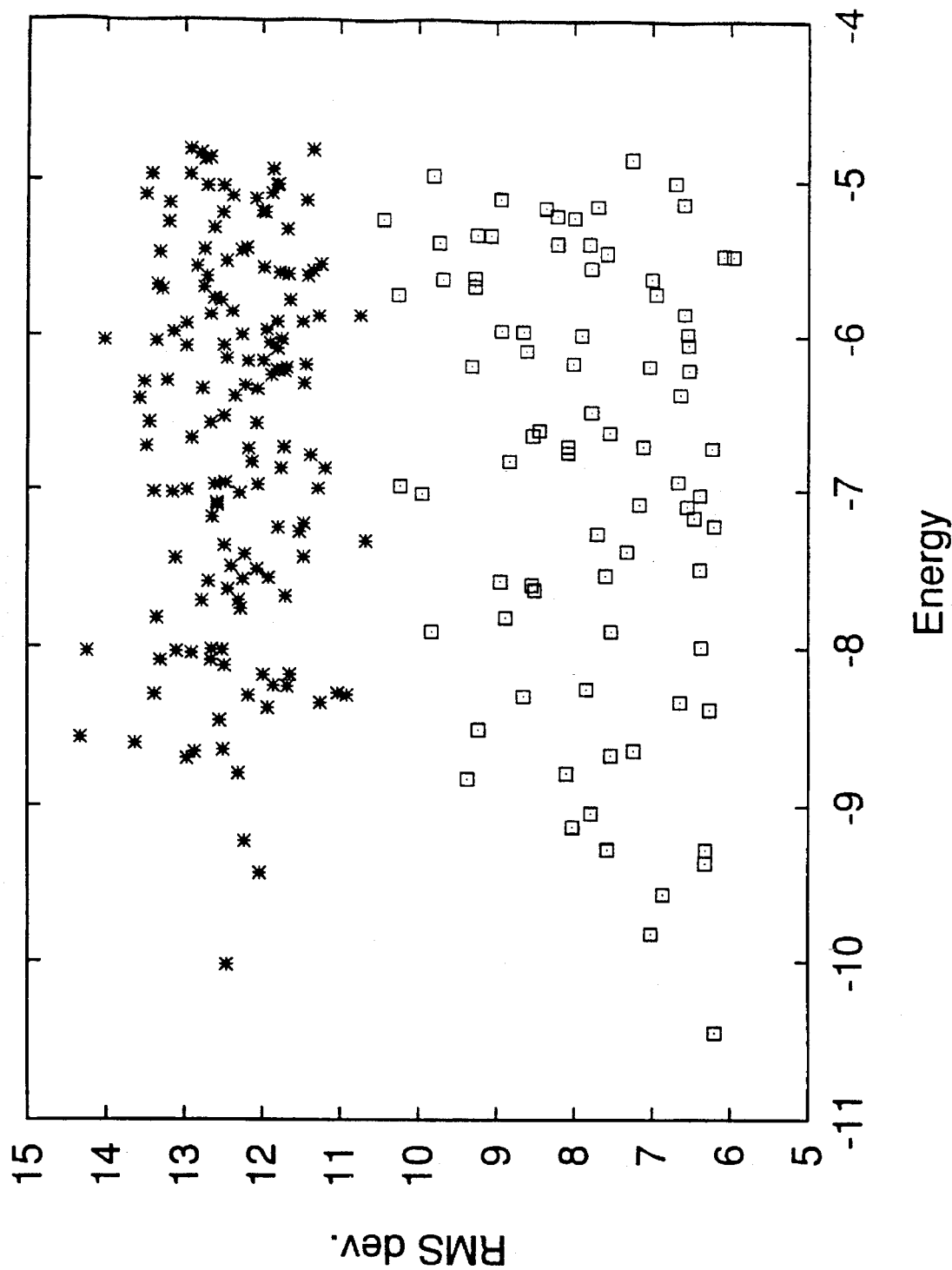
FIG. 6 shows two clusters of low-energy structures from the ensemble shown in FIG. 5, indicated by the different symbols. See text for further discussion.

Additional analysis of the final ensemble clearly demonstrates the clustering of structures. The 256 distinct structures lowest in energy were selected and the r.m.s. deviation was calculated between all pairs. Pairs which had r.m.s. deviations of less the 5 Å were defined to be in the same cluster, and therefore also any pair for which there exists a third structure less than 5 Å from both, and so on. The largest two clusters identified in this way, consisting of 146 and 82 structures, are shown in FIG. 6 by stars and squares, respectively. The remaining 28 structures were greater than 5 Å from any of those shown, and were grouped into an additional 16 clusters, each with fewer than five members. The average deviation between members of the same cluster is 6.1 Å and 5.8 Å, respectively, for the first two clusters, and the average between the two clusters is 12.2 Å. This result is remarkable in that no reference was made to the native structure in the cluster selection, and yet this procedure cleanly isolates those structures which have the lowest r.m.s. deviation from the native. This suggests that the clusters of structures generated by the simulation do indeed represent distinct folded topologies, one of which is clearly native-like within the resolution of the model.

Figure 7:
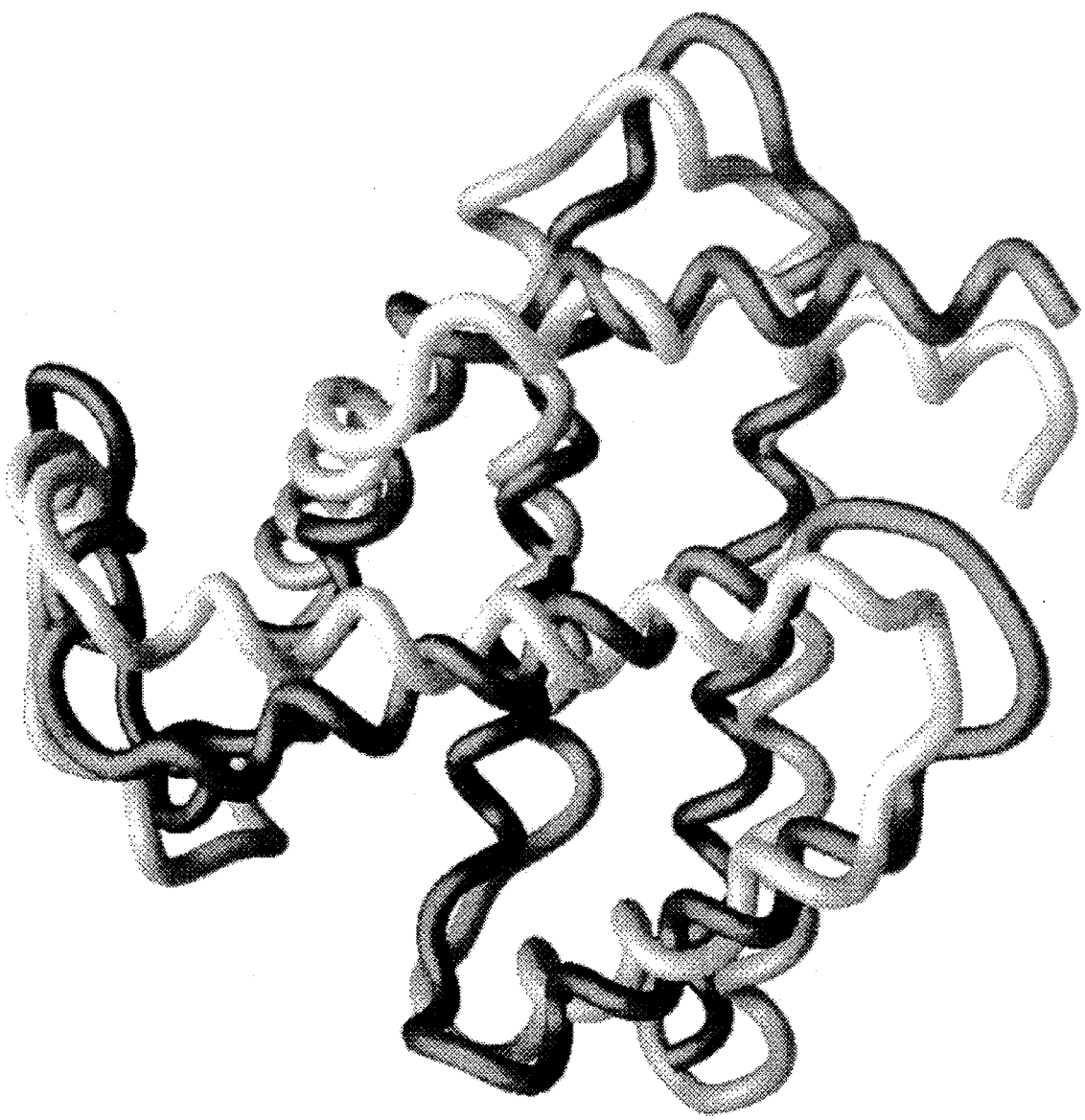
FIG. 7 shows α-carbon backbone worm structures for the native (light) and calculated (dark) conformations of myoglobin shown in the optimal superposition with 6.2 Å r.m.s. deviation.
Figure 8:
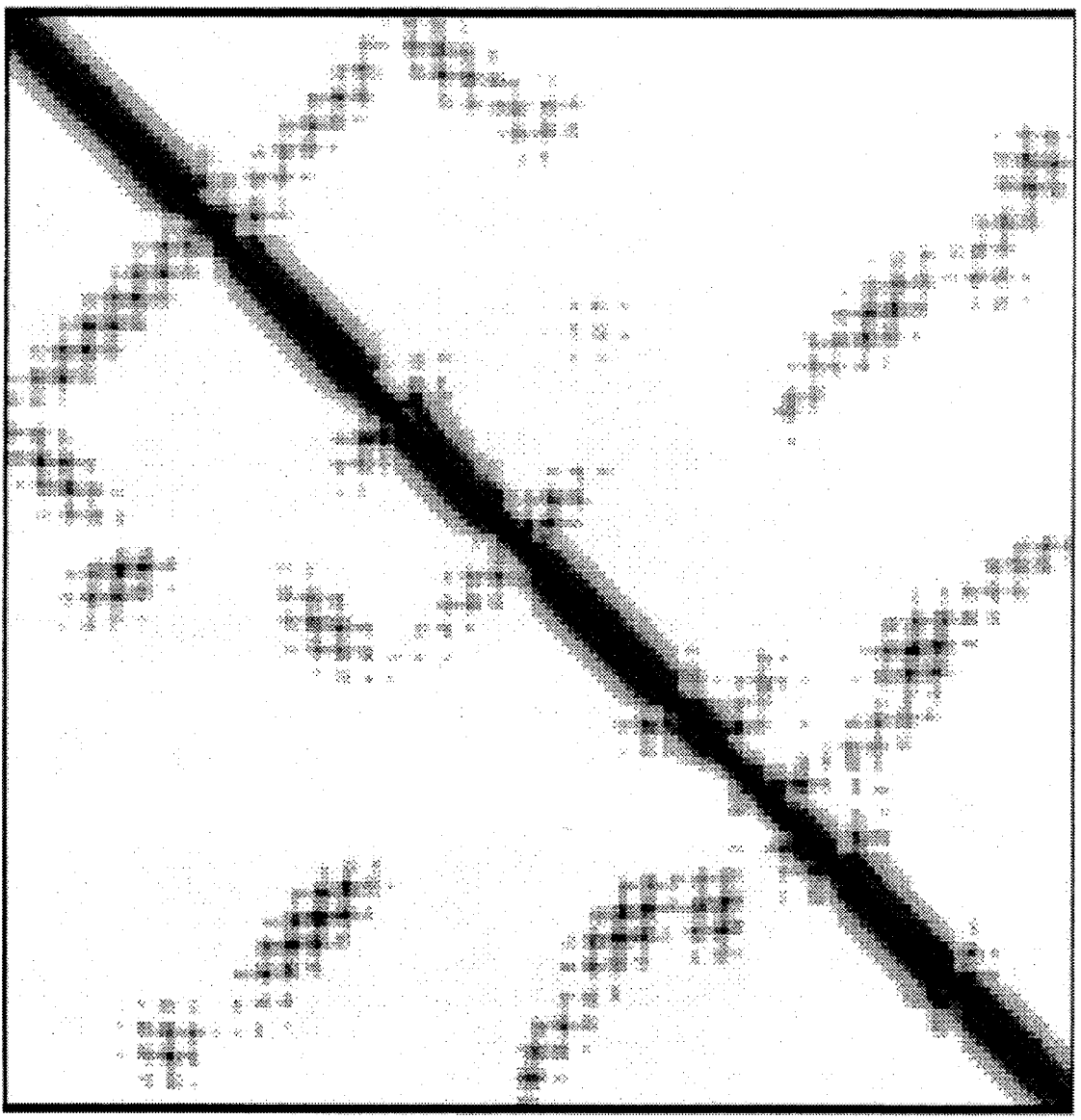
FIG. 8 shows residue-residue distance maps for the native (upper) and calculated (lower) conformations of myoglobin. Shading indicates $C_\beta$ distances of <3 Å (dark to >10 Å (light). Structures are the same as in FIG. 7.

The lowest energy structure at this stage has an r.m.s. deviation of 6.2 Å from the native $C_\alpha$ coordinates taken from the Protein Data Bank, and an energy of −10.5 equal to that of the native in arbitrary units. This structure is shown in FIG. 7, superimposed on the native conformation. The agreement is good within the original cylinder and sphere picture of the molecule. Further improvement could be expected by relaxing the constraints of ideal bond angles and discrete dihedral angles. However, at this level of description the native tertiary structure has been recovered almost completely. The major source of error in the structure is in the loop regions, and is expected since the model is based on the assumption that the structure is dominated by the packing of the helices. The potential is relatively insensitive to the detailed structure of the loops which are selected essentially on the basis of their overall geometries which determine the relative orientations of the adjacent helices. If only the six helices consisting of three or more turns are included in the calculation of the r.m.s. deviation the result is 4.1 Å for the 103 remaining residues. As a further evaluation of the structure, the inter-residue distance map is shown in FIG. 8 juxtaposed with that of the native structure. This shows that all regions of helix-helix contact found in the native are reproduced in the calculated structure. Although some are more or less pronounced and may be slightly offset in the sequence, this demonstrates that the folded topology is essentially correct. This is another indication that the sources of error in the calculation are those regions of the molecule which contribute relatively little to the total energy with such a simple potential function.

Figure 9:
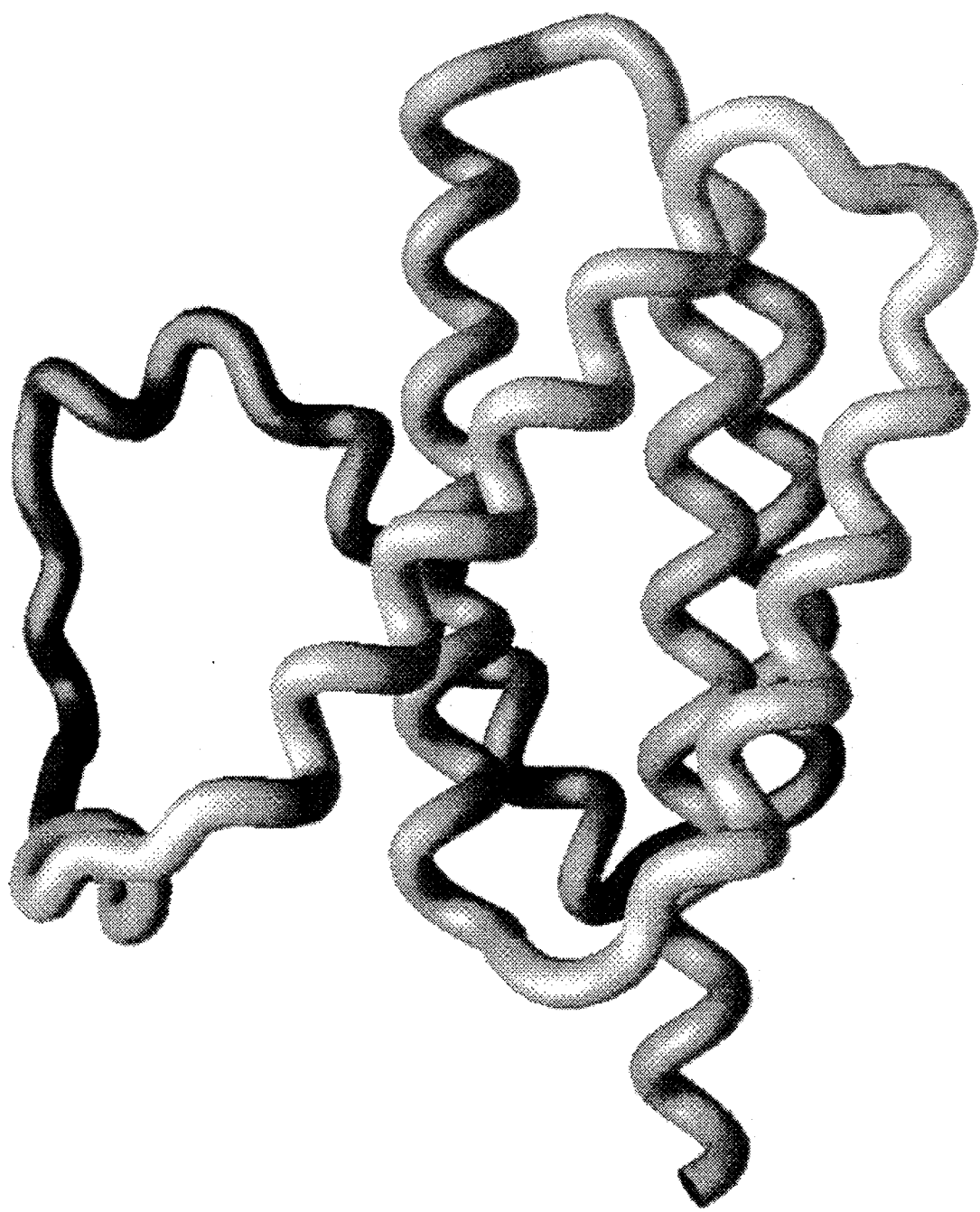
FIG. 9 shows an α-carbon backbone worm structure of a misfolded conformation of myoglobin with 12.5 Å r.m.s. deviation.
Figure 10:
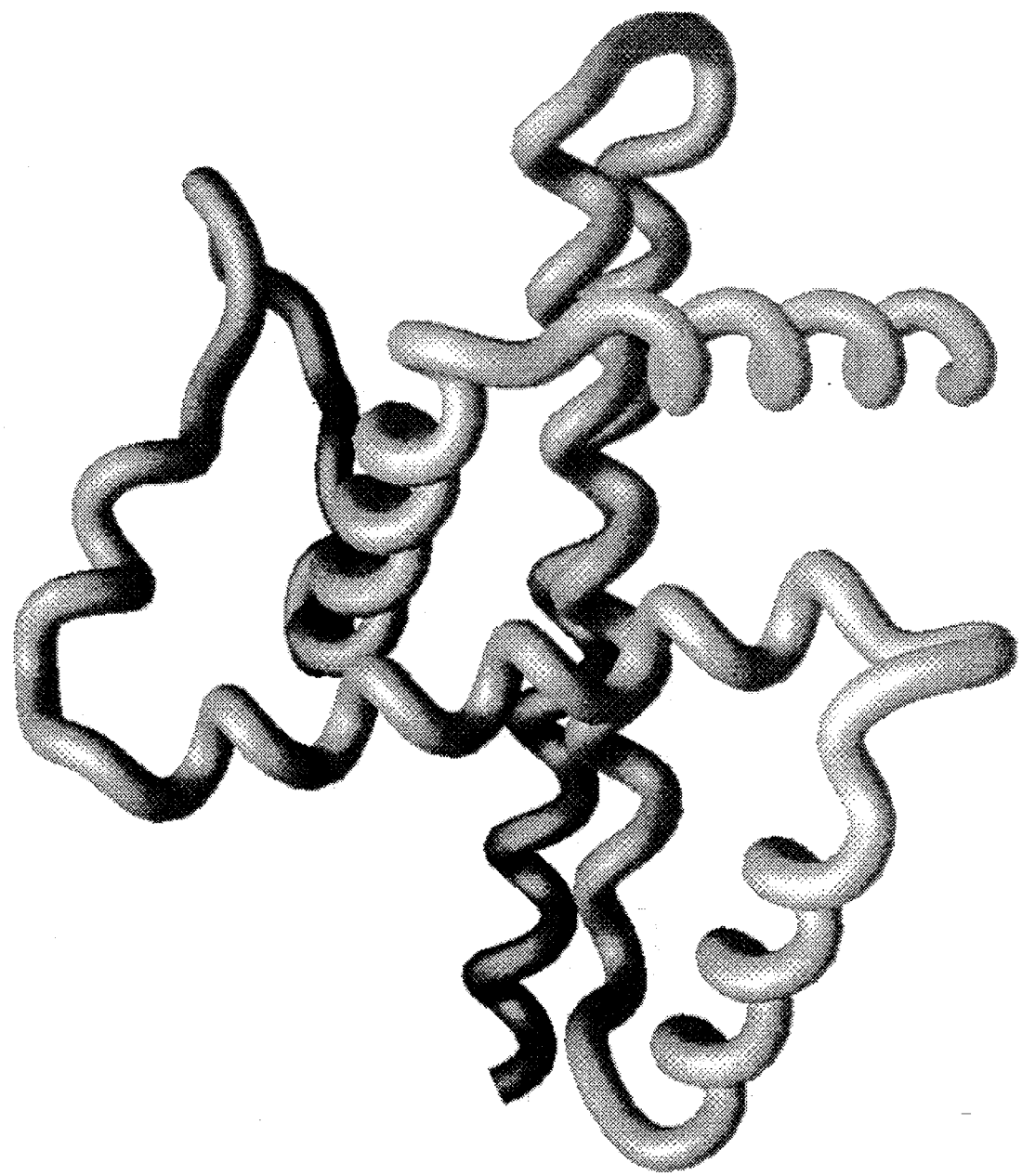
FIG. 10 shows an α-carbon backbone worm structure of a misfolded conformation of myoglobin with 8.7 Å r.m.s. deviation.
Figure 11:
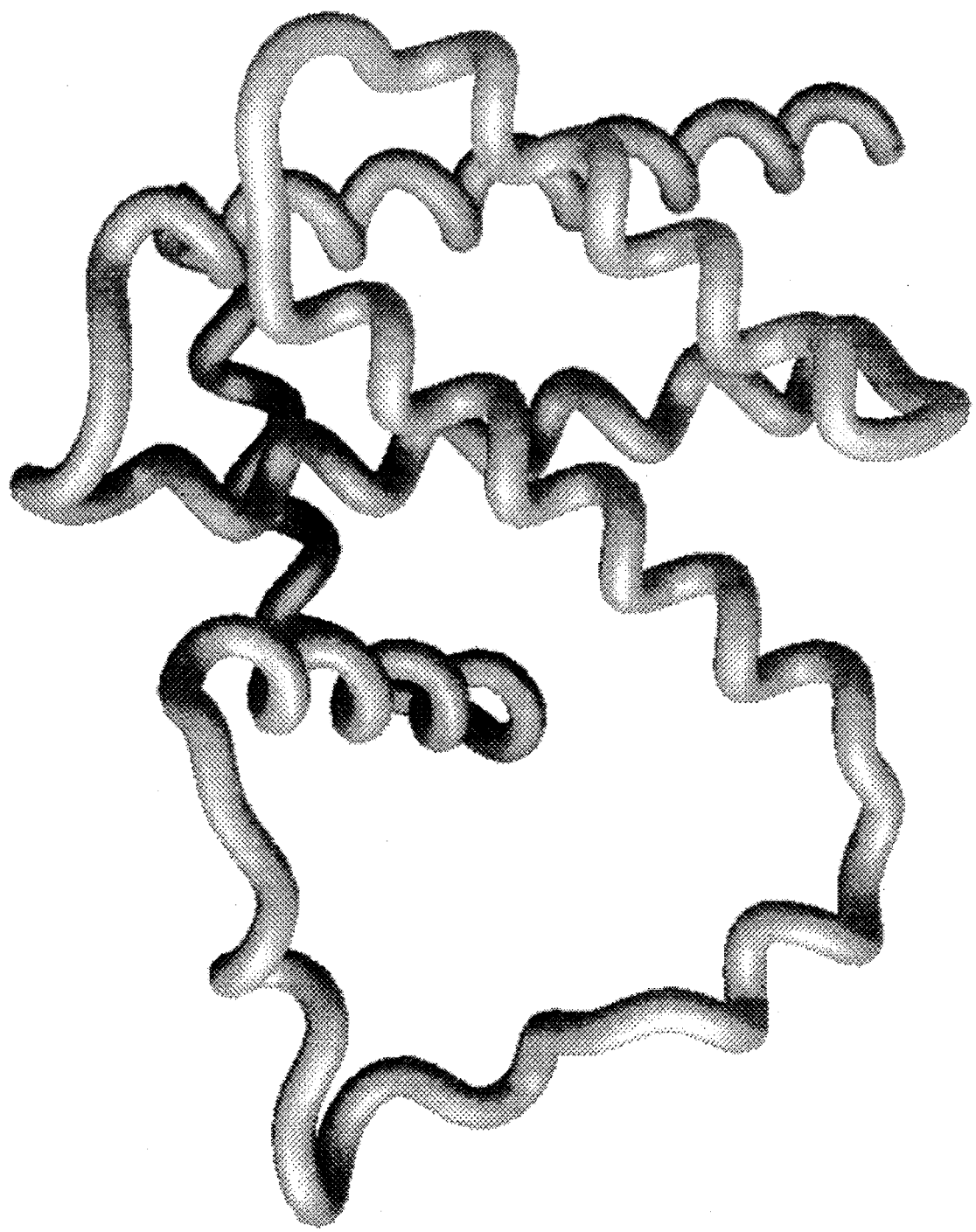
FIG. 11 shows an α-carbon backbone worm structure of a misfolded conformation of myoglobin with 11.7 Å r.m.s. deviation.

The structure of the lowest energy configuration from the second cluster of structures is shown in FIG. 9 with an r.m.s. of 12.5 Å and an energy of −10.0. This structure is slightly more compact than the native and seems like a reasonable guess at the structure. Many of the individual loop configurations are in fact quite similar to those found in the native. This suggests than many aspects of the structure are likely reproduced fairly consistently throughout the ensemble. Additional simulations were carried out on independent ensembles in order to verify the above observations. In each case some structures were generated with 7 Å or less r.m.s. deviation, but most were not among the low-energy structures. The same types of misfolded structures were also seen, but the details of which had the lower energies and which clusters of structures were dominant varied from simulation to simulation. This suggests that the results may depend on specific loop geometries being included in the ensemble which produce low-energy structural elements. Since the sampling of loops is random and nowhere near exhaustive, the low-energy representatives of the common folded topologies will vary from run to run. An additional cluster of low-energy structures was found with r.m.s. deviations of around 8–9 Å which look essentially native-like but with one or two helices misaligned. An example of a structure with an r.m.s. deviation of 8.7 Å and an energy of −10.3 is shown in FIG. 10 which shows the two longer helices rotated out of the correct position. The lowest energy structure generated in any calculation with an energy of −11.8 and an r.m.s. deviation of 11.7 Å is shown in FIG. 11. Again, it can be seen that the structure shares many features with the other low-energy examples.

It has been previously calculated that a randomly generated structure of myoglobin with the native secondary structure subject to a constraining sphere would have an average r.m.s. deviation of 16.2 Å which is larger than any of the final structures generated by the simulation.[15] This suggests that even the misfolded structures generally contain important elements of the structure. Such 'intelligently' misfolded structures provide a much greater test of the potential function than previous comparisons which typically involved superimposing the native sequence on the folded structures of completely different proteins. A more sophisticated model will be required in order to distinguish these structures reliably. Therefore, the goal of the simulation is to ensure that the native-like topology is at least one of a small number of distinct low-energy conformations. It is not known whether these other structures are the result of using such a simple model to describe the molecule or represent real local minima in the potential surface of myoglobin.

IV—Conclusion

The present invention demonstrates use of an algorithm which is capable of generating folded structures of specified secondary structural units. Trial simulations of myoglobin have produced structures that are essentially native within the resolution of the model. It has been estimated that the chances of randomly producing structures of comparable r.m.s. deviation from the native are roughly $10^{-13}$.[15] The appearance of such structures in some simulations therefore demonstrates the efficiency of the sampling techniques.

The results provided hereinabove indicate that there are several different folded topologies which are comparable in energy, and that the potential function used in the present simulations is not capable of accurately differentiating them. Due to the discrete representation of the residue conformations, the structures are only approximations to the local minima of the potential, so that for any given simulation the native structure may or may not be the lowest in energy.

Further resolution can be obtained by screening the lower energy structures against a partial set of experimentally determined distance constraints or by further theoretical methods. A small number of the structures produced in the simulation could be optimized using a more sophisticated model which can correctly identify the native topology as well reduce the deviation of the calculated structure by relaxing the constraints on the dihedral angles.

The method disclosed herein can be easily generalized to treat β-strands, so that proteins containing virtually arbitrary combinations of helices, loops, and strands can be predicted.

The results of the present work suggest a number of interesting physical hypotheses. First, it is apparently the case that the internal energies of the loop regions (e.g. torsional energies) play a minimal role in the topological formation of myoglobin (and perhaps most globular proteins), as the results provided hereinabove were achieved without any local potential other than the exclusion of inaccessible regions of the Ramachandran map. Instead, packing and hydrophobicity of the helices control the basic structural features and the loops deform themselves to produce the optimal arrangement. There are of course many loop geometries for long loops which have the same endpoint topology, and local energetics may have more effect in selecting among these conformers; the r.m.s. deviations for the 11-membered loop are by far the most substantial obtained.

A second question is raised in considering the distribution of structures and energies obtained herein. There are numerous conformations which have small r.m.s. deviations from the native structure but which also have very high energies according to the model potential (which produced structures with deviations as small as 3.9 Å in this class, by minimizing the r.m.s. directly). Typically, these structures also have a radius of gyration that is ≈1 Å larger than the native structure, or the best low-energy structures. Assuming that the potential function is roughly correct for these structures, This suggests that in the in vivo folding process the system cycles through a wide range of 'blown up' topologies and that only the native is capable of collapsing to the final folded state. This sort of picture can be contrasted with a more extensive sort of funneling in which native-like topologies are preferred early on due to long-range (e.g., electrostatic) fields. Of course, these observations may also be an artifact of the potential.

In addition, although it is known experimentally that myoglobin folds to roughly the same structure in the absence of the prosthetic heme group, [16] it is not clear what structural changes do result. In the structure generated by the simulations with low r.m.s. deviation from the native, the largest source of error is in the region of the heme binding site. It seems likely that the details of this structure are stabilized by interaction with the heme which are not present in the model provided herein. It may be the case, in fact, that the structures generated by the simulation may be lower in energy than the native, and consequently closer to the true structure of apomyoglobin.

References
1. Covell, D. G.; Jernigan, R. L. *Biochemistry* 1990 29, 3287–3294; Hinds, D. A.; Levitt, M. *Proc. Natl. Acad. Sci. USA* 1992 89, 2536–2540; Sun, S. *Protein Sci.* 1993 2, 762–785.
2. Skolnick, J.; Kolinski, A. *Science* 1990 250, 1121–1125; Kolinsky, A.; Skolnick, J. *J. Chem. Phys.* 1993 98, 7420–7433.
3. Bashford, D; Cohen, F. E.; Karplus, M.; Kuntz, I. D.; Weaver, D. L. *Proteins Struct. Funct. Genet.* 1988 4, 211–227.
4. Kim, P. S.; Baldwin, R. L.; *Ann, Rev. Biochem.* 1982 51, 459–489; Dyson, H. J.; Merutka, G.; Waltho, J. P.; Lerner, R. A.; Wright, P. E. *J Mol. Biol.* 1992 226, 795–817; Dyson, H. J.; Sayre, J. R.; Merutka, G.; Shin, H.-C.; Lerner, R. A.; Wright, P. E. *J. Mol. Biol.* 1992 226, 819–835.
5. Levitt, M.; Warshel, A. *Nature* 1975 253, 694–698.
6. Cohen, F. E.; Richmond, T. J.; Richards, F. M. *J. Mol. Biol.* 1979 132, 275–288.
7. Monge, A.; Friesher, R. A.; Honig, B. sumbitted to *Proc. Natl. Acad, Sci. USA*
8. Johnson, L. A., Monge, A.; Friesher, R. A. *J. Chem Phys.* 1992 97, 9355–9365.
9. Rooman, M. J.; Kocher, J. A.; Wodak, S. J. *J. Mol. Biol.* 1991 221, 961–979.
10. Casari, G.; Sippl, M. J. *J. Mol. Biol.* 1992 224, 725–732.
11. Maiorov, V. N.; Crippen, G. M. *J. Mol. Biol.* 1992 227, 876–888.
12. Unger, R.; Moult, J. *J. Mol. Biol.* 1993 231, 75–81.
13. Liu, Z. H.; Berne, B. J., preprint.

14. Kostrowski, J.; Scheraga, H. A. *J. Phys. Chem.* 1992 96, 7442–7449; Roitberg, A.; Elber, R. *J. Chem. Phys.* 1991 95, 9277–9287.
15. Cohen, F. E.; Sternberg, M. J. E. *J. Mol. Biol.* 1980 138, 321–333.
16. Neya, S.; Funasaki, N.; Sato, T.; Igarashi, N.; Tanaka, N. *J. Biol. Chem.* 1993 268, 8935–8942.

What is claimed is:

1. A method for determining the most stable tertiary structure of a protein having a known primary structure which comprises the steps of (a) producing a reduced representation of the protein by assigning to the protein (i) secondary structural motifs comprising loops and helices present therein and (ii) all $\phi$ and $\Phi$ dihedral angles for the amino acid residues present therein; (b) determining which conformations of the reduced representation are physically permissible (c) determining which of the physically permissible conformations of the protein possesses the lowest free energy which comprises the steps of (i) randomly varying the dihedral angles of each conformation and evaluating energy for each conformation using a dipole approximation, (ii) accepting or rejecting a conformation in accordance with Metropolis test criteria, (iii) iterating steps (c)(i) and (ii) on accepted conformations and generating $C_\alpha$ and if present $C_\beta$ atomic coordinates for all residues, and (iv) evaluating energy using the atomic coordinates and a full potential function for all conformations to provide an ensemble of low energy conformations; and (d) comparing conformations to determine that of lowest energy, so as to thereby determine the most stable tertiary structure of the protein.

2. The method of claim 1 wherein secondary structural motifs in step (a)(i) are helical initially with each residue contained by a cylinder and with cylinders for all residues collinear to ensure a globally extended geometry.

3. The method of claim 1 wherein all secondary structural motifs in step (a)(i) are helical initially with each residue contained by a cylinder, and determining the physically permissible conformations in step (b) comprises selecting a loop with values of internal coordinates from a look-up table of loop geometries, and rotating the cylinders according to the values of internal coordinates for each loop selected.

4. The method of claim 3 wherein each loop geometry is generated by simultaneously constructing an array of random loops of a given length and repeating such construction until all loops necessary to conform with the assigned secondary structural motifs in the protein are accepted.

5. The method of claim 4 wherein each conformation is checked for self-avoidance using cylinders containing secondary structural motifs which are helical and spheres enclosing the loops to reject structures which are not physically permissible.

6. The method of claim 5 wherein $C_\alpha$ and if present $C_\beta$ coordinates are generated for about four residues on either side of each loop.

7. The method of claim 1 wherein in determining whether each reduced representation is accepted or rejected in step (c)(ii), the Metropolis test is carried out at a constant 'bath' temperature corresponding to an average error of approximation.

8. The method of claim 1 wherein certain residues overlap in a physically permissible reduced representation generated in step (c), and such overlapping residues are calculated from $C_\alpha$ and if present $C_\beta$ atomic coordinates, and wherein a constant penalty is added to the energy to provide a combined energy and penalty for the representation, which is accepted or rejected in accord with the Metropolis test using the combined energy and penalty.

* * * * *